United States Patent
Lee et al.

(10) Patent No.: US 7,001,426 B2
(45) Date of Patent: Feb. 21, 2006

(54) ONE-PIECE MINICAPSULORHEXIS VALVE

(75) Inventors: William Lee, Miami, FL (US); Viviana Fernandez, Miami, FL (US); Jean-Marie Parel, Miami Shores, FL (US); Arthur Ho, Randwick (AU)

(73) Assignee: The Institute for Eye Research, Sydney (AU)

( * ) Notice: Subject to any disclaimer, the term of this patent is extended or adjusted under 35 U.S.C. 154(b) by 210 days.

(21) Appl. No.: 10/298,964

(22) Filed: Nov. 18, 2002

(65) Prior Publication Data

US 2004/0098122 A1    May 20, 2004

(51) Int. Cl.
*A61F 2/14*    (2006.01)
(52) U.S. Cl. ..................................... 623/4.1
(58) Field of Classification Search ............. 623/4.1, 623/6.38–6.41
See application file for complete search history.

(56) References Cited

U.S. PATENT DOCUMENTS

| | | |
|---|---|---|
| 4,002,169 A | 1/1977 | Cupler, II |
| 5,391,590 A | 2/1995 | Gerace et al. |
| 5,474,282 A | 12/1995 | Eckert |
| 6,358,279 B1 | 3/2002 | Tahi et al. |
| 2002/0107567 A1 | 8/2002 | Terwee et al. |

FOREIGN PATENT DOCUMENTS

FR    2 745 711 A    9/1997

OTHER PUBLICATIONS

Nishi et al., "Accomodation Amplitude After Lens Refilling with Injectable Silicone by Sealing the Capsule with a Plug in Primates", *Arch Ophthalmol*, 1998, pp. 1358-1361, vol. 116.
Nishi et al., "Anterior Capsule-Supported Intraocular Lens", *Graefe's Arch. Clin. Exp. Ophthalmol*, 1990, pp. 582-588, vol. 228.
International Search Report issued in International Patent Application No. PCT/US03/35992.

*Primary Examiner*—Corrine McDermott
*Assistant Examiner*—William Matthews
(74) *Attorney, Agent, or Firm*—Kilpatrick Stockton LLP; David M. Krasnow

(57) ABSTRACT

A one-piece capsulorhexis device is presented comprising a membrane having a curved, flexible substantially discoid flap-valve member shaped to align with an ocular lens capsular bag inner surface, and at least one integral, flexible retainer shaped to align with an ocular lens capsular bag outer surface.

14 Claims, 11 Drawing Sheets

ONE-PIECE MINICAPSULORHEXIS VALVE

FIELD OF THE INVENTION

The invention relates to a unitary minicapsulorhexis valve (MCV) device comprising a flexible discoid flap-valve member and a flexible retainer, the device serving to seal a capsulorhexis opening created during ocular interventions.

BACKGROUND OF THE INVENTION

The human eye, comprises a roughly spherical organ having essentially three distinct layers of tissue, divided into three basic chambers. The tough outer sclerotic coat serves as a protective barrier for the eye, and forms the transparent cornea through which light passes into the eye. The sclerotic coat is composed of dense collagenous tissue. The middle choroid coat forms the iris, a diaphragm that controls the amount of light admitted into the interior of the eye through the pupil. Immediately posterior to the iris is the transparent crystalline lens, held in place by zonular fibers attached to ciliary processes surrounding the crystalline lens. The zonular fibers collectively culminate in the suspensory ligament of the lens. The region between the cornea and crystalline lens is denoted the anterior chamber of the eye, whereas the gap created between portions of the crystalline lens and iris is known as the posterior chamber. Ciliary processes generate aqueous humor, which fills the anterior chamber and posterior chamber. Aqueous humor provides for nutrient and metabolic exchange between the avascular cornea, crystalline lens, and iris. The posterior pole of the crystalline lens abuts the hyaloid fossa of the posterior vitreous chamber of the eye. Accommodation, the process of changing the focus of the eye between distant and near objects, is achieved by constriction and relaxation of the ciliary muscle connected to the crystalline lens via the zonular ligament. Such movement by the ciliary muscle serves to shape the crystalline lens to the appropriate optical configuration for focussing light rays from these objects onto the inner coat of the eye, structurally known as the retina.

The crystalline lens is a biconvex body, having an anterior convexity less steep and of a greater radius of curvature than its more parabolic posterior convexity. The lens is composed of elongated, prismatic cells known as lens fibers, which are tightly packed to form lamellar structures. Intracellular granular crystallins within the lens fibers confer upon the lens its transparent and refractive characteristics. Lens fiber structure and composition varies within the lens such that a firm central nucleus may be distinguished from a softer surrounding cortex. The entire lens is encompassed by the lens capsule (capsula lentis), a basement membrane into which the zonular fibers are inserted. The elastic lens capsule is composed of collagen fibers, glycosaminoglycans and glycoproteins. Due to its elastic properties, the lens capsule can stretch substantially in circumference without tearing.

A variety of disorders are known to impair or destroy normal function of the eye, including disorders of the lens, such as cataracts and presbyopia. Cataracts arise from progressive clouding of the crystalline lens, which, if left untreated, eventually obscure light rays from focussing on the retina. Historically, cataracts were surgically treated by either intracapsular removal of the entire lens structure, including the outer lens capsule and the inner crystalline lens matter, or extracapsular removal of the central portion of the anterior capsule and the crystalline lens matter, leaving in place the posterior lens capsule, known in the art as the ECCE procedure. These procedures are prone to complications, such as retinal detachment, and, in the case of extracapsular cataract extraction, opacification of the posterior capsule.

Recently developed lens refilling procedures may reduce the incidence of many complications associated with traditional cataract treatment modalities. One such procedure is disclosed in U.S. Pat. No. 4,002,169, in which a rotary masticating tool is introduced into the lens structure via an inserted hollow needle. The capsular tissue contents, including the cataract, lens cortex and lens nucleus, are physically liquefied and then withdrawn from the lens capsule via suction through the needle. Such a process leaves the lens capsule intact as a capsular bag within the posterior chamber.

Often, a chemical treatment or sonication (phacoemulsification) is preferred over physical mastication for liquefying the lens. Following suction removal of the liquefied crystalline lens, the capsular bag may be flushed to remove remaining debris and then refilled with a molded synthetic lens, as disclosed in U.S. Pat. No. 5,674,282.

Alternatively, a new lens may be created in situ with a filler material having the appropriate characteristics to mimic the function of the natural crystalline lens. Many ophthalmic procedures designed to restore accommodation of the eye, such as lens refilling procedures for the correction of presbyopia and cataracts, rely on the replacement of endogenous lens matrix material with a transparent material of similar consistency and index of refraction and spectra.

Some of the preferred materials for filling the capsular bag comprise UV-curable polymers that require exposure to ultraviolet light to induce crosslinking. Such crosslinking typically requires two openings be created in the wall of the eye via bimanual surgery, which occupies both hands of the ophthalmic surgeon. Alternatively, crosslinking may be effected through the cornea, but such procedures may damage corneal tissues.

Intraocular lenses may comprise relatively hard materials, relatively soft materials, or a combination of both types of materials. For example, methyl methacrylates, polysulfones or other relatively hard, biologically inert optical materials may be used alone, or in combination with softer biologically inert silicones, hydrogels or semi-rigid thermolabile materials.

U.S. Pat. No. 5,391,590 discloses compositions useful as injectable intraocular lens material. Examples of polymerizable formulations include one or more polyorganosiloxanes having a vinyl functionality, a silicon-bonded hydride group, and the like. Such compositions may comprise soft, fast curing, low temperature vulcanization silicone gels capable of in situ polymerization within the capsular bag. High molecular weight, high viscosity silicone precursor fluids are preferred, as they are less likely to leak from the injection site prior to polymerization. Such high viscosity materials only require a low cross-linking density to achieve an elastic modulus similar to a human crystalline lens. However, a reduced cross-linking density of these polymers results in an unacceptable gummy product having low resilience.

Certain low viscosity, low molecular weight fluids have desirable properties upon cure for injectable ocular lenses, but readily leak from the injection site. Upon curing of leaked gel, a bump may form on the surface of a refilled capsule. Such bumps are known to irritate the iris and mediate corneal edema. In an attempt to overcome this limitation, suitable low molecular weight fluids may be pre-cured to induce polymerization prior to injection into the lens capsular bag. Injection of such partially polymerized materials through a cannula may cause shear stress, which results in rough areas of the polymerized material that impair the function of the synthetic lens. Additionally, pre-cured polymer materials typically must be injected shortly after initiating crosslinking to prevent over-curing and reduced flow through the cannula, making such materials awkward to use.

Typically, the capsular bag tends to under fill unless very high density materials, such as gels having a viscosity of greater than 4 Mcts, are used. As mentioned hereinabove, viscous liquids and gels introduced into the capsular bag for this purpose often leak from the bag, particularly when fluids having less than 1 Mcts viscosity or soft gels are injected.

Leakage of such materials into the anterior chamber of the eye may cause a number of ocular problems, and endanger delicate ocular structures. For example, intraocular inflammation may be spurred by a foreign body reaction of the eye in response to the leaked material. Additionally, leaching of non-endogenous liquids or gels from the capsular bag may cause glaucoma, due to blockade of trabeculac and associated increases in intraocular pressure due to increased volumes of aqueous humor. Undesirable conditions, such as interference with motion of the iris and impairment of the optics of the eye due to glare are also known to occur upon escape of viscous liquids and gels introduced to the capsular bag.

Similarly, cataract surgery may require the introduction of a chemical agent to liquefy nuclear matter, and/or injection of a chemical or pharmacological agent to kill lens epithelial cells or impair their replication. Leakage of antimitotic compounds or hypoosmolar solutions destroys healthy, non-regenerative corneal endothelial and retinal cells of the eye, as opposed to the intended hyperproliferative lens epithelium.

An anterior capsulotomy, specifically a capsulorhexis, is typically used to reduce some of the procedural and post-operative complications associated with extracapsular and lens refilling protocols. A continuous tear capsulorhexis involves preparing a circular or round capsulotomy in the anterior lens capsule, forming an essentially circular tear line substantially coaxial with the lens axis, in cases of ECCE and peripherally in the case of lens refilling, and removing the essentially circular portion of the anterior capsule delineated by the continuous tear line. Preferably, the capsulotomy is positioned within the zonule-free area of the anterior lens capsule. This type of capsulotomy forms a circular opening in the anterior lens capsule, through which cataractous lens matrix may be extracted by, for example, phacoemulsification and aspiration. What remains is a capsular bag having an elastic posterior capsule, an anterior capsular remnant about the anterior capsulotomy, and an annular capsular bag sulcus between the anterior capsule remnant and the outer circumference of the posterior capsule. Thus, the capsular bag remains attached to the surrounding ciliary muscle of the eye via the zonules, and is responsive to ciliary contraction and relaxation during accommodation.

Although continuous tear capsulorhexis is designed to provide an anterior capsule remnant or rim having a relatively smooth, continuous inner edge abutting the capsulotomy, the anterior rim is sometimes torn, radially sliced, or nicked during this procedure. Such damage to the anterior rim leaves the rim vulnerable to tearing radially when the rim is stressed, particularly upon insertion of instruments for manipulating the capsular lens matrix. Tearing of the lens capsule during capsulorhexis increases the likelihood of untoward leakage of materials injected into the evacuated capsular bag during lens refilling. To reduce the risk of such tearing, a deep anterior chamber is maintained throughout the surgery using a balanced salt solution or a viscoelastic material to fill the chamber. However, tears may arise despite taking such precautionary measures.

In an effort to address some of these ongoing problems in ophthalmic surgery, Nishi et al. (*Graefe's Arch Clin Exp Ophthamol* (1990) 228:582–588) developed a new lens for small-incision surgery, which also serves to seal the capsular opening. Following a circular mini-capsulorhexis and phacoemulsification procedures, an acrylamide synthetic lens larger than the capsular opening is inserted into the opening. After injecting a visco-elastic material into the capsular bag and anterior chamber of the eye, the lens is inserted into the anterior chamber. The lens is then manipulated such that the lens is choked by the entire capsular margin along its circumference, thereby fixing the lens in place of the missing portion of anterior capsule. Since the lens seals the opening of the lens capsule, the lens capsular bag is capable of refilling. Thus, a replacement material, polyacrylamide gel, is injected into the capsular bag to expand the bag. Although generally successful, certain drawbacks exist with this process, including expansion of the capsulorhexis opening during filling, causing intraoperative leakage. Moreover, Nishi et al. reported difficulties achieving a reproducible, centrally positioned circular capsulorhexis of an appropriate size for securely holding the inserted synthetic lens in the capsular bag. Furthermore, patients receiving such intraocular lens implantation may develop capsular bag distention causing blurred vision.

Nishi and Nishi (*Arch Ophthalmol* (1998) 116(10):1358–1361) recently devised a tube having a flange made to fit a surgically generated capsulorhexis opening in a patient's capsular bag. This tube is permanently bonded to the edges of the capsulorhexis with a silicone-based adhesive, meaning the device is an implant. Thereafter, a clear gel is injected through the tube via a 30 gauge stainless steel cannula. After filling the capsular bag, an adhesive within the tube seals the tube. The tube is then cut to remove excess length, although the remaining tube slightly protrudes from the bag into the anterior chamber of the eye. The protrusion of this implant may mechanically interfere with motion of the iris, impairing pupillary opening and closing. Contact of the inner surface of the iris causes drag, which may interfere with ocular accommodation. In addition, the protruding tube may scratch the corneal endothelium upon rubbing of the patient's eye containing the implant. Such implants are susceptible to biocompatibility problems, and may cause severe inflammatory reactions within the eye.

One MCV device was designed as a two-piece device with each piece connected with an adhesive. See commonly owned U.S. Pat. No. 6,358,279, which is incorporated by reference as if made a part of the specification herein. However, potential complications exist with these two-piece devices. It is often difficult to obtain devices having a uniform thickness for forming two uniform pieces. Additionally, it is difficult to accurately, reproducibly and safely bond the two elements of the two-piece device. Further, such bonding materials or procedures also can contribute to the aforementioned biocompatibility problems. Still further, the two-piece MCV constructions may delay regulatory approval or make the product otherwise commercially undesirable.

SUMMARY OF THE INVENTION

In one embodiment the present invention is directed to a unitary, or one-piece capsulorhexis valve device comprising a flexible discoid flap-valve member, preferably shaped to align with an ocular lens capsular bag inner surface. The device further comprises at least one integral flexible retainer, preferably shaped and dimensioned to align with an ocular lens capsular bag outer surface.

In another embodiment, the present invention is directed to a unitary capsulorhexis valve device comprising a membrane made from a material transparent to radiation. The membrane preferably has a wavelength transmission of from about 300 nm to about 1100 nm, with the material made from a biocompatible elastomer selected from the group consisting of urethanes, silicones, crosslinkable-terminated trimethyl polydimethylsiloxanes, crosslinkable-terminated dimethyldiphenylsiloxanes, collagen, collagen derivatives, hydrogels and mixtures thereof. Examples of preferred hydrogels include poly-acrylamides, poly-N-vinylpyrrolidones, hydroxyalkylacrylates such as HEMA (hydroxyethylmethacrylate), and poly-tetrafluoroethylene (PTFE), polyethylene (PE), and poly-ethyleneglycol diacrylate (PEGDA). The membrane has a discoid portion and at least one integral retainer with the retainer extending radially outward from the discoid portion.

In yet another embodiment, the present invention is directed to a method of accessing an ocular lens. An incision is made in the limbus to open an anterior chamber of an eye. The chamber is then filled with a viscoelastic solution. An anterior capsulorhexis opening is made in the lens capsule. A unitary flexible capsulorhexis valve device is then inserted into the capsulorhexis. The device comprises a discoid portion having a periphery, and at least one integral flexible retainer such that the periphery of the device is positioned along an interior surface of the lens capsule and said flexible retainer is positioned along an outer surface of the lens capsule, thus positioning a wall of the lens capsule therebetween.

In yet another embodiment, the present invention is also directed to a method of accessing an ocular lens comprising making a limbus incision to open an anterior chamber of an eye and filling the anterior chamber with a viscoelastic solution. Thereafter, an anterior capsulorhexis opening is created in a lens capsule, into which is inserted a MCV device comprising a flexible flap-valve portion and a flexible retaining member. The MCV device is inserted such that said flexible flap-valve portion of the MCV is positioned along an interior surface of the lens capsule and said flexible retaining feature is positioned along an outer surface of the lens capsule, compressing a wall of the lens capsule therebetween. The MCV device is then released to establish a portal controlling access to an ocular lens. The method may further comprise the steps of inserting a cannula through the MCV device to permit removal of a crystalline lens matrix and replacement thereof with a capsular filling material.

The present invention is further directed to a method of accessing an ocular lens in which a MCV device acts as a valve or seal to prevent leakage of antimitotic or cytotoxic agents during interoperative lavage and the refilling of a capsular bag.

BRIEF DESCRIPTION OF THE DRAWINGS

Having thus described the invention in general terms, reference will now be made to the accompanying drawings, which are not necessarily drawn to scale, and wherein

Figure 1A:
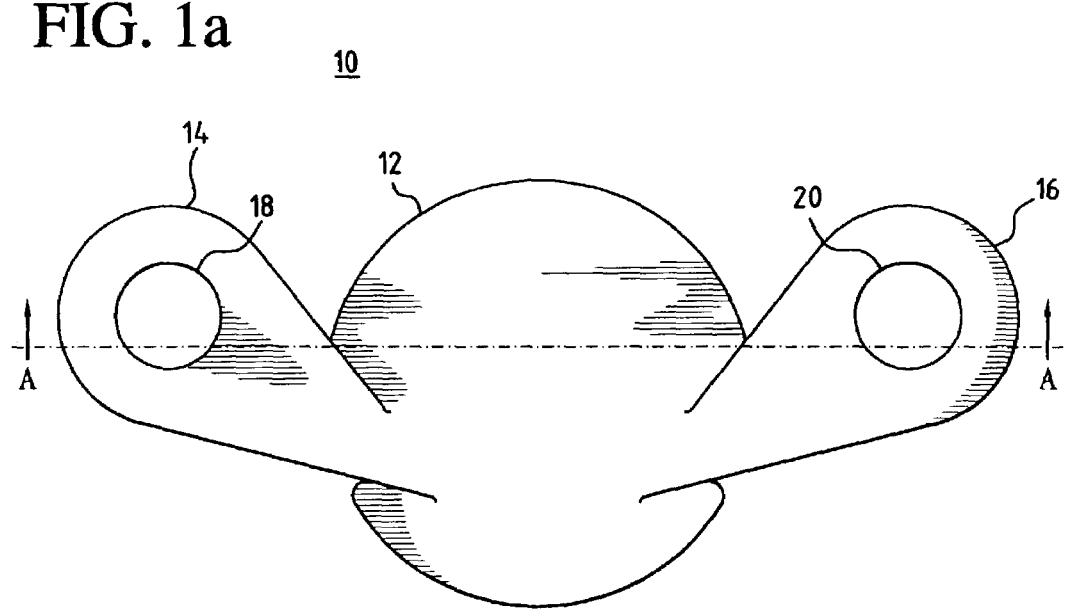
Figure 1B:
Figure 1C:
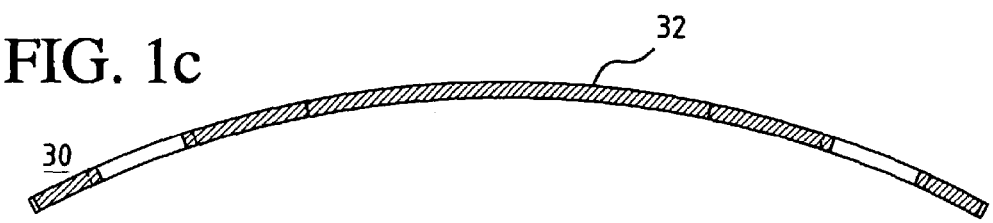
Figure 2:
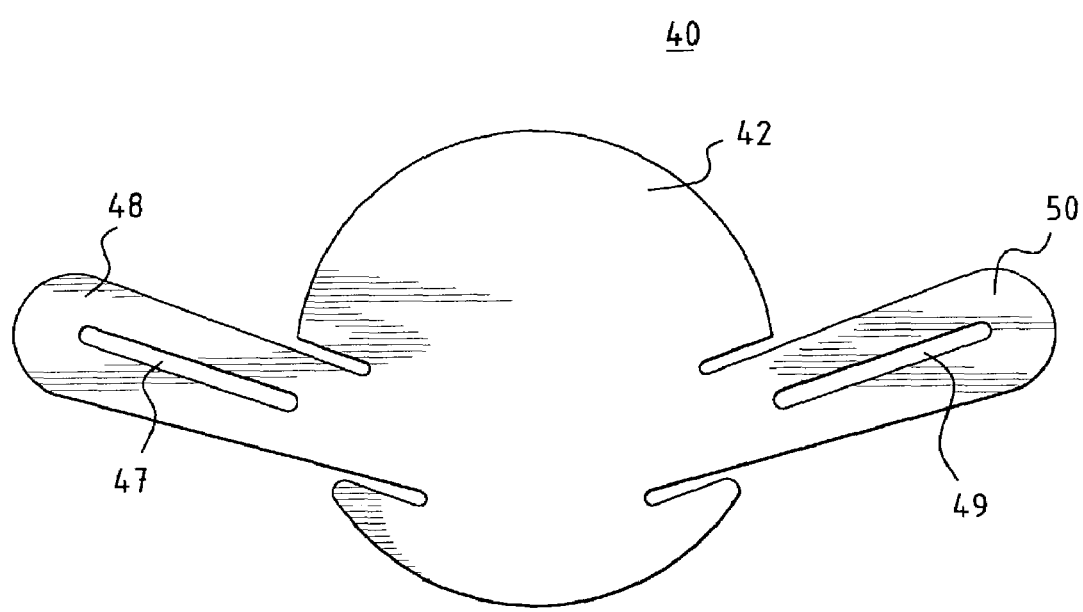
Figure 3:
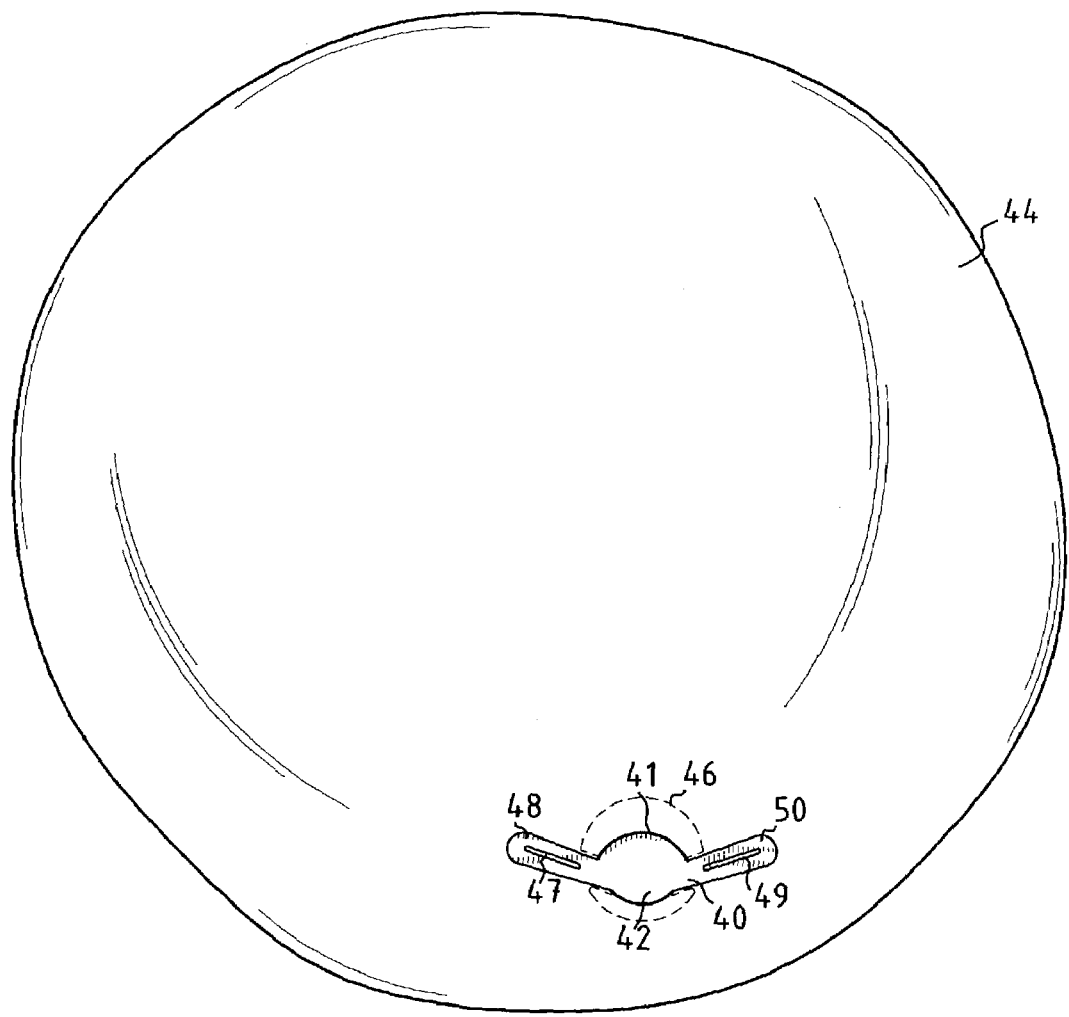
Figure 4:
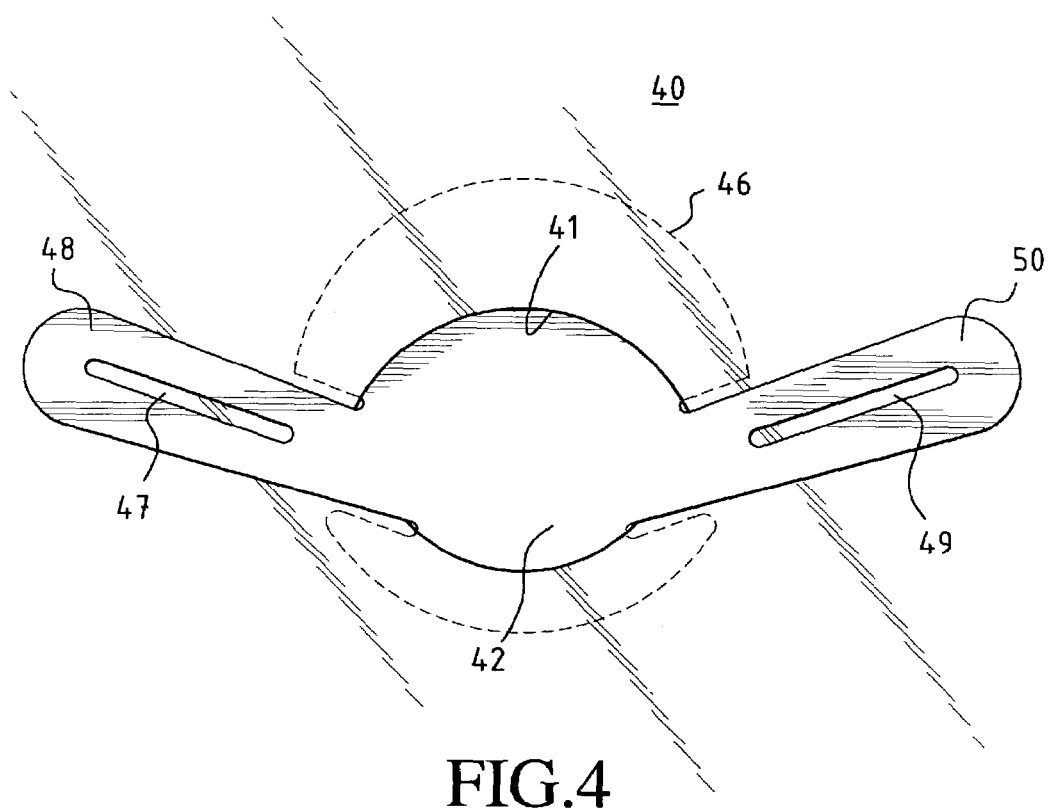
Figure 5A:
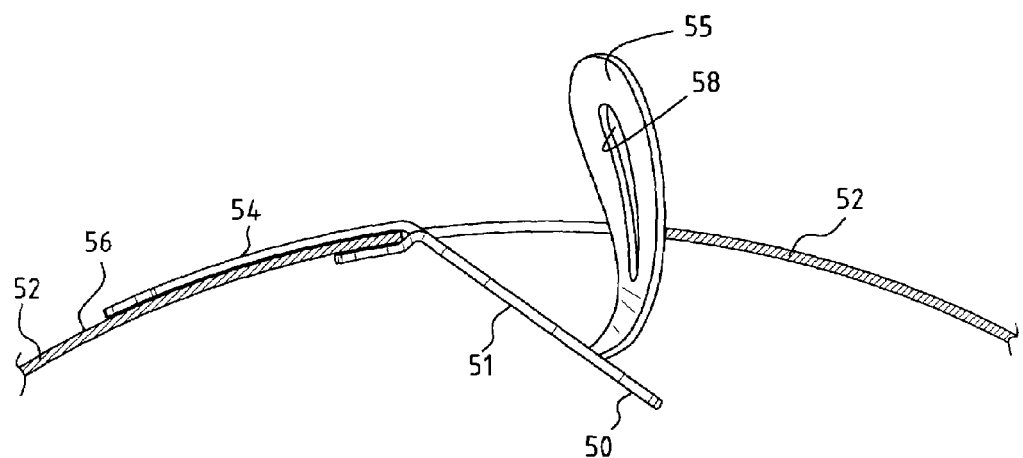
Figure 5B:
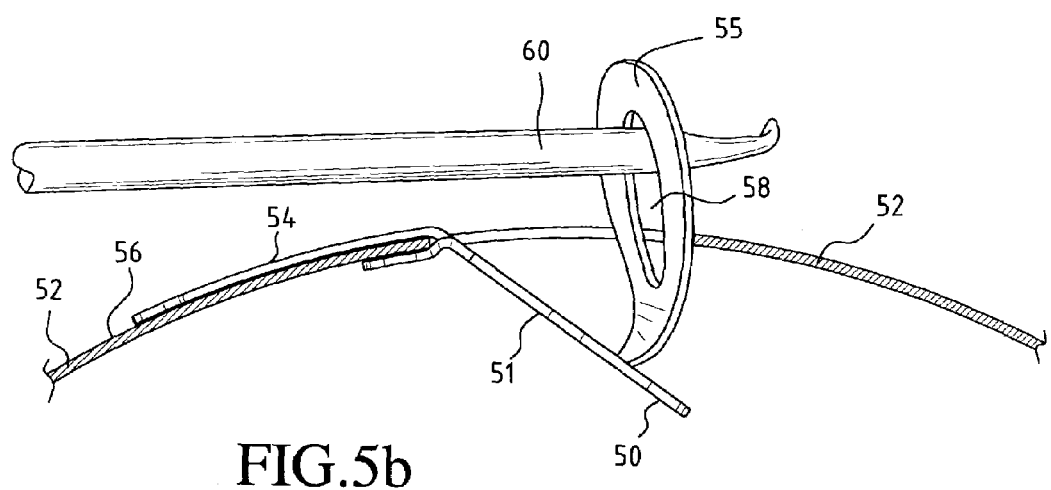
Figure 6:
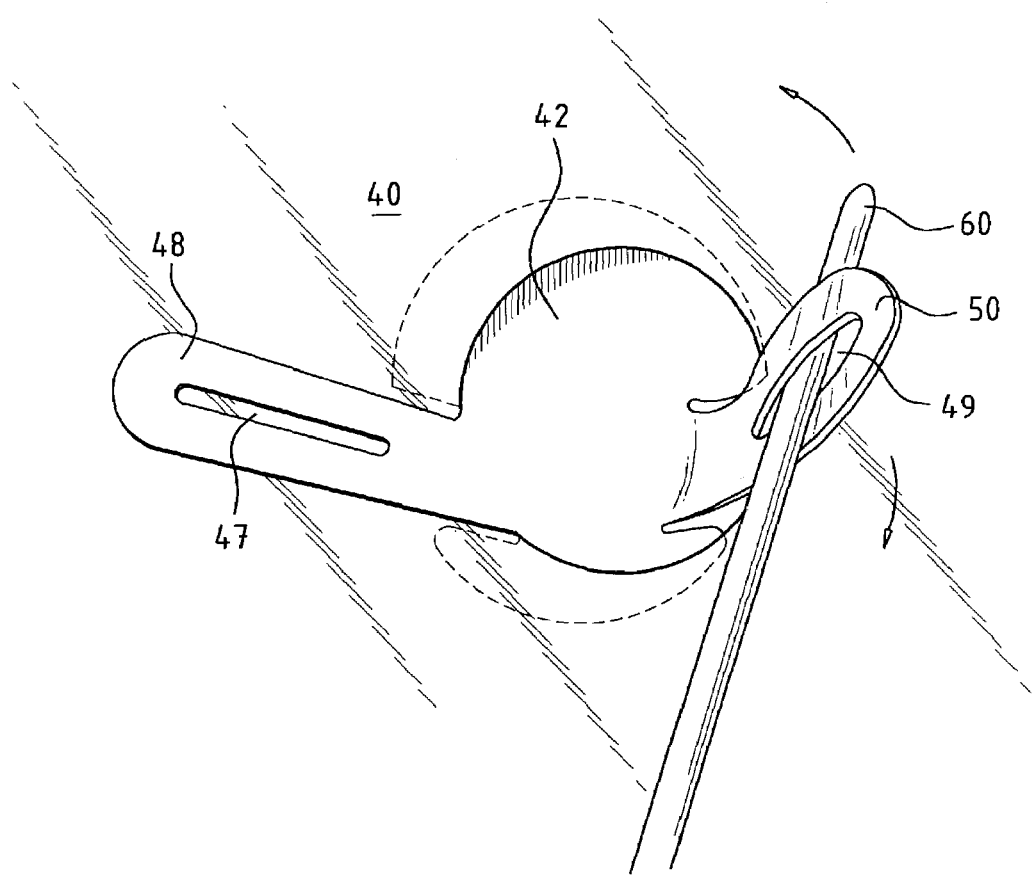
Figure 7:
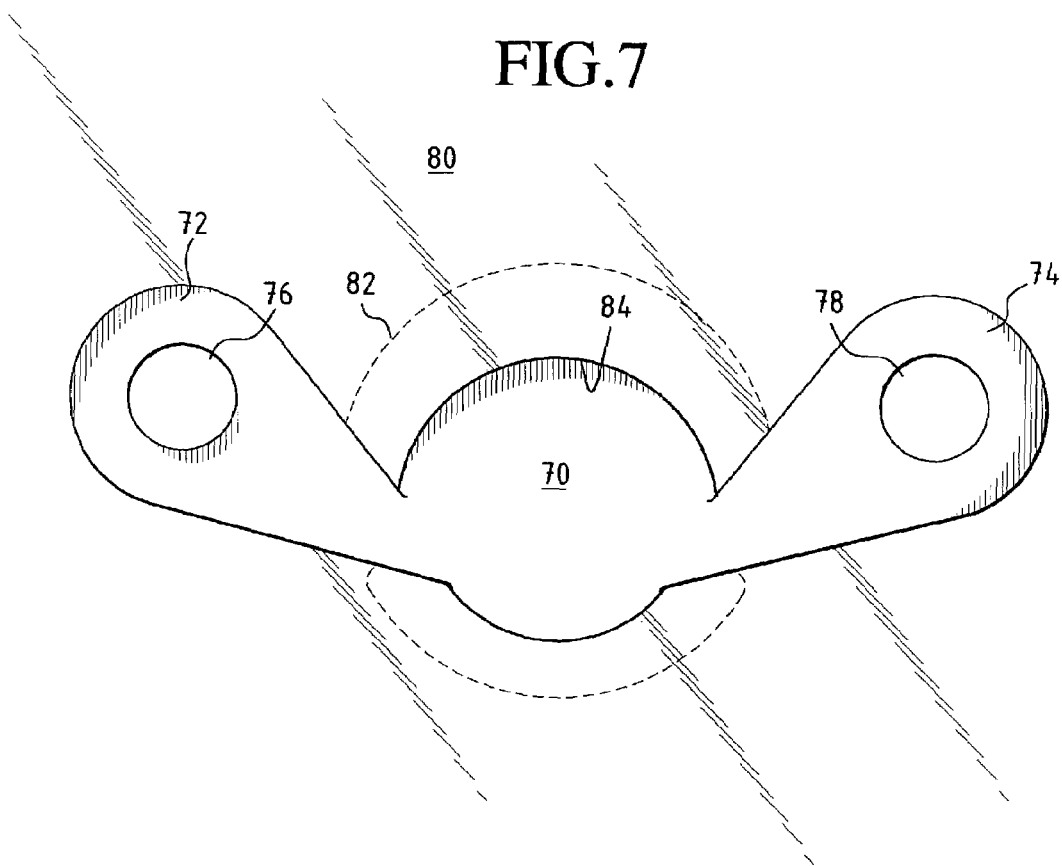
Figure 8:
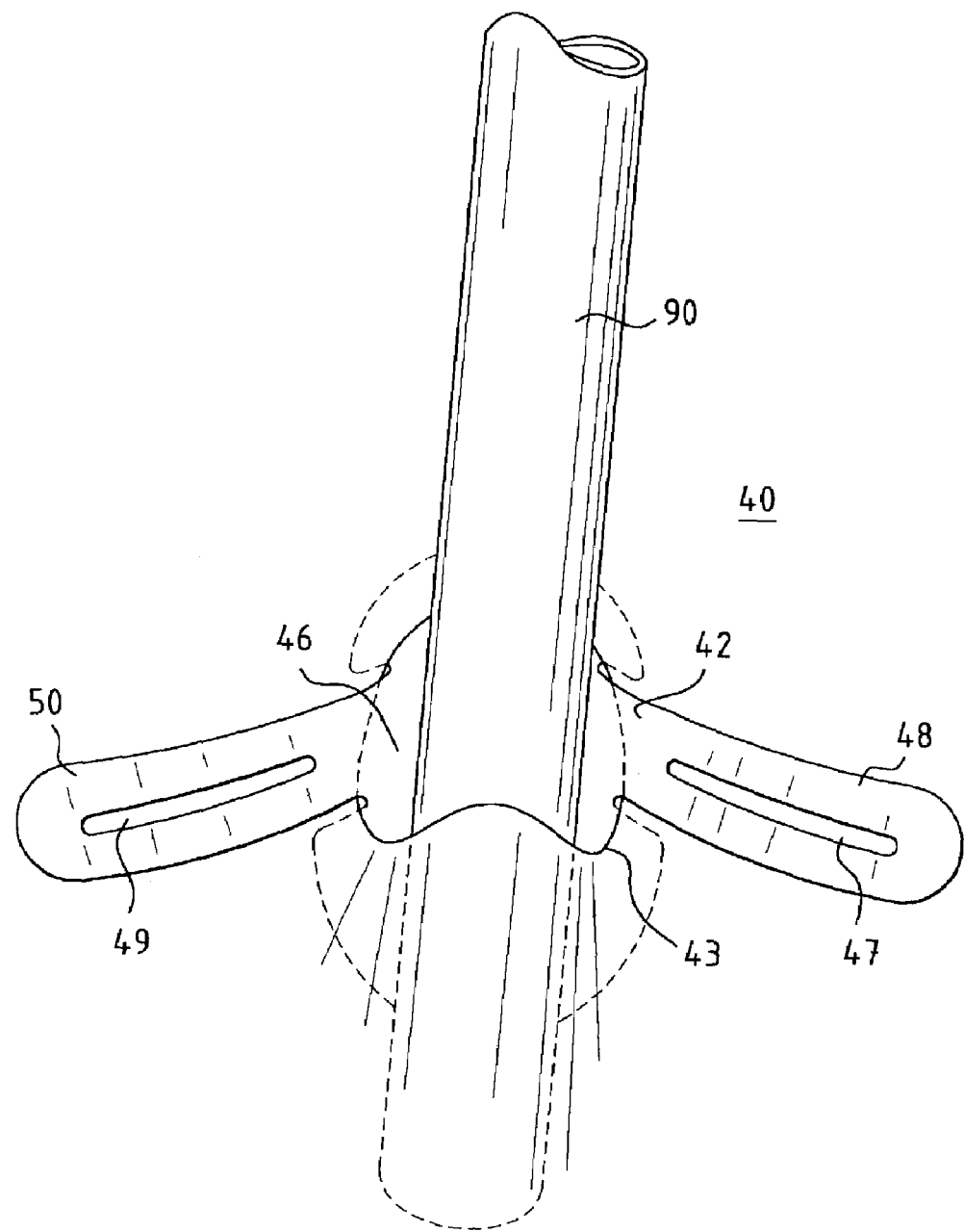
Figure 9:
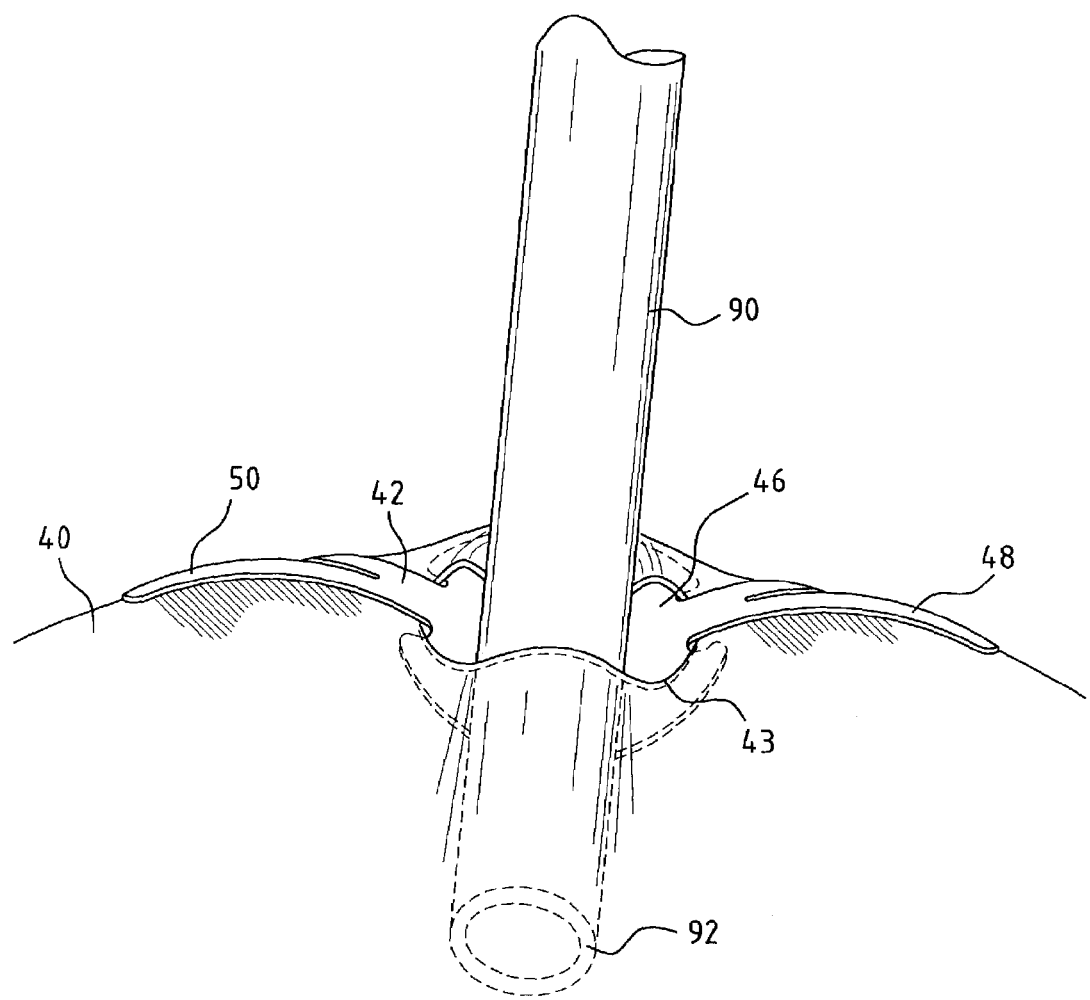
Figure 10:
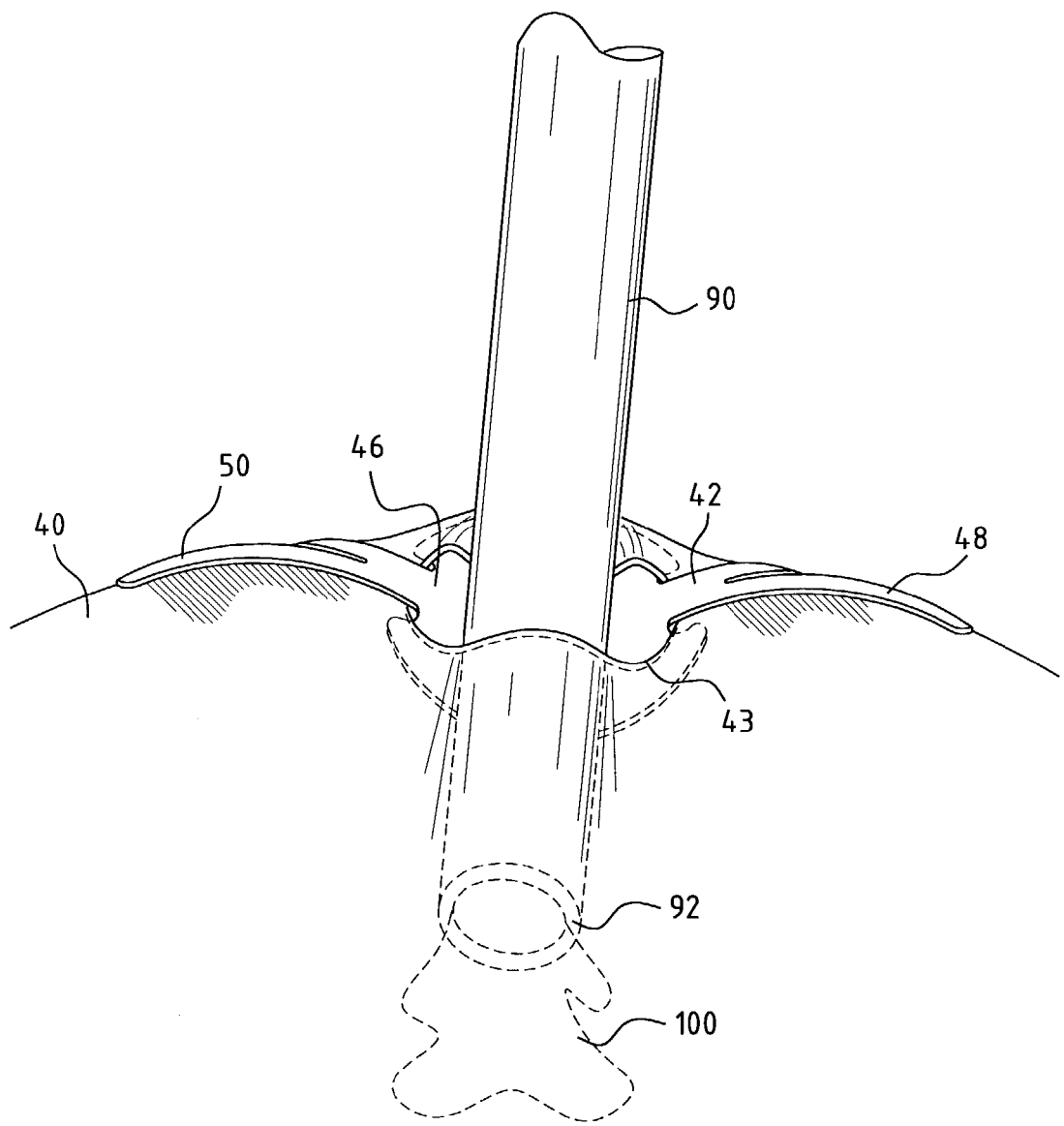
Figure 11A:
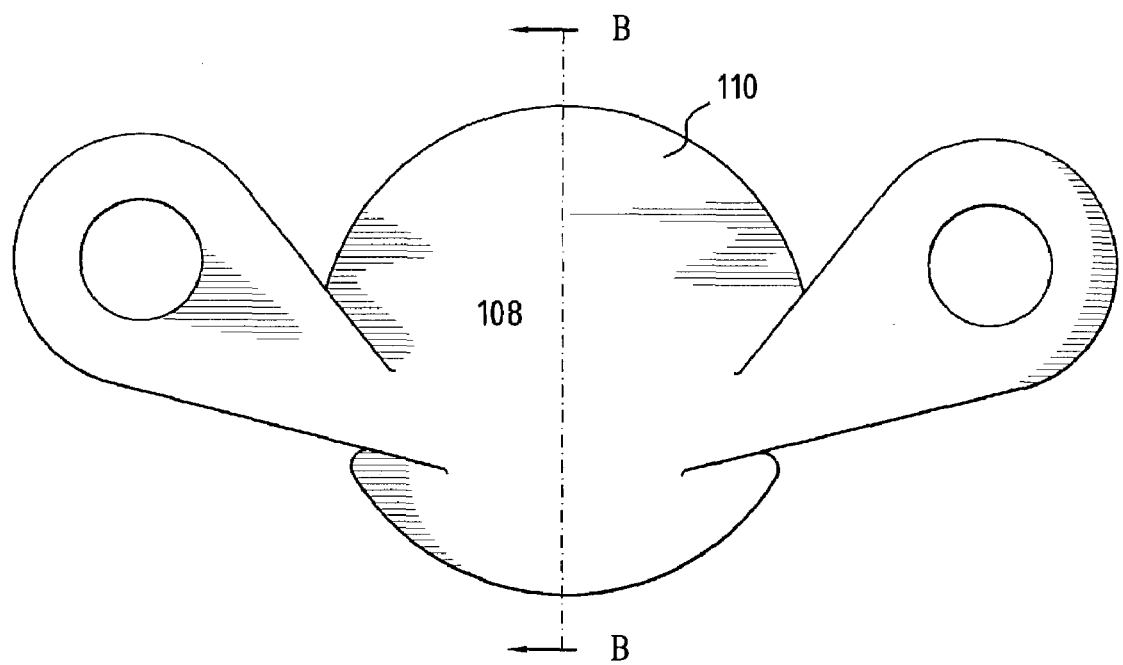
Figure 11B:
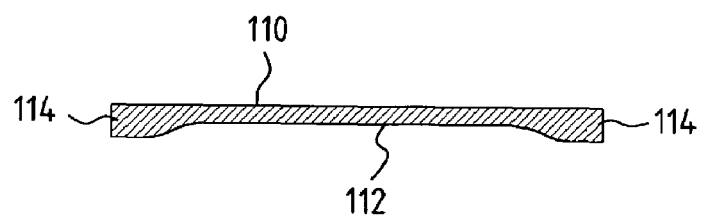

FIG. 1a shows a top plan view of the MCV device of the present invention;

FIG. 1b shows a cross-sectional side view of one preferred embodiment of the MVC;

FIG. 1c shows a cross-sectional side view of another embodiment of the MCV, which has a curvature dimensioned to approximate the capsule's natural curvature;

FIG. 2 shows an embodiment of the present invention whereby the MCV retainer arms are substantially oblong;

FIGS. 3–4 respectively show a plan view and an enlarged view of the MCV device of FIG. 2 inserted into the capsular bag of an eye;

FIGS. 5a–5b show cross-sectional side views of one embodiment of the present invention, an MCV being positioned at the surface to cover an opening;

FIG. 6 shows plan views of one embodiment of the MCV of the present invention being positioned to substantially cover an opening, the MCV having substantially oblong retainer arms;

FIG. 7 shows an embodiment of the present invention whereby the apertures in the retainer arms are circular and the retainer arms are substantially teardrop-shaped;

FIGS. 8–10 show one embodiment of the present invention with a cannula in place to effect filling the lens capsule; and FIGS. 11a–11b respectively show a plan view and a cross-sectional side view of an embodiment of the present invention whereby the circular discoid portion of the MCV is thinner than the circular periphery.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

In a preferred embodiment of the invention, as shown in FIG. 1a, a unitary MCV valve device 10 comprises a single, thin, flexible, and preferably elastic membrane shaped such that it has a discoid portion 12 and substantially teardrop-shaped retainer arms 14, 16. Substantially circular apertures 18, 20 in arms 14, 16 respectively assist in the positioning of the device. FIG. 1b shows a cross-sectional side view of the MCV of FIG. 1a across line A—A. According to the present invention, the MCV may be designed to be flat, or may be designed to be curved to substantially match the curvature of a membrane to be sealed, such as, for example a capsular bag. Therefore, FIG. 1c is a cross-sectional side view of an MCV 30 designed to have a curvature on the outer, or posterior MCV surface 32 that substantially matches the curve on the inner or anterior surface or a membrane to be sealed (not shown), such as, for example a capsular bag.

FIG. 2 shows another embodiment of the present invention where MCV 40 has a discoid section 42 and substantially slit-like apertures 47, 49 in substantially oblong retainer arms 48, 50 respectively.

FIG. 3 shows the device of FIG. 2 whereby MCV 40 is positioned within a capsulorhexis opening 41 in a capsular bag 44. Dotted line 46 represents the perimeter of the MCV 40 that extends beneath the anterior surface of the capsular bag 44. Retainer arms 48, 50 rest on the outer surface of the capsular bag. In other words, for the MCV to seal the opening in the capsular bag, the perimeter of the capsulorhexis opening preferably rests between the retainer arms 48, 50 and the perimeter of the discoid section 42 of the MCV. FIG. 4 is an enlarged view of the MCV 40 of FIGS. 2–3.

FIGS. 5a and 5b are cross-sectional side views showing MCV 50 of the present invention being inserted into position in a capsular bag 52. In FIG. 5a, retainer arm 54 is shown in position resting on the outer surface 56 of bag 52. Retainer arm 55 as shown is not yet in final position. In FIG. 5b positioning tool 60 is shown engaging retaining arm 55 through aperture 58. In this way, the positioning tool 60 will direct the necessary upward force supplied, for example, by a human or a machine to pull the retaining arm and the connected discoid portion of the MCV 50 into position. Therefore, upon insertion into a capsulorhexis opening in a capsular bag 52, discoid portion 51 of MCV 50 is oriented at least partially within the capsular bag 52, while retainers 54, 55 are situated exteriorly to the outer surface 56 of capsule 52, such that the capsule wall 52 is disposed therebetween. The diameter of the discoid portion 51 of the MCV 50 is selected to be slightly larger than the diameter of the capsulorhexis opening to more than completely fill the void of the opening. To insure proper positioning and retention of the MCV, the length of the retainers 54, 55 is greater than the capsulorhexis, and preferably about twice as great. The integral retainers 54, 55 serve as a mechanical brace to support and predictably position the flexible discoid member 51.

Preferably, the discoid portion of the MCV has a curved shape to align with the capsular bag inner surface. See FIG. 1c. However, a thin, flexible MCV with a substantially flat portion of the type shown in FIGS. 5a and 5b also has been shown to work well. Still further, the discoid portion may not be circular in shape but may be, for example, oval, rectangular with rounded corners, "pear-shaped" or irregularly shaped. Preferably retainer arms are curved to substantially match the curvature of the anterior (outer) surface of the capsular bag. As shown, retainers 54, 55 are arched in a vertical dimension to avoid mechanical interference with the iris. It is understood, however, that thin flat MCVs without substantial curvature may conform adequately to the surface to which they are applied as the capsule is substantially flat when empty after extraction and the pressure from within the capsule by the gel when it is refilled renders both the flexible MCV and capsule curved.

FIG. 6 shows an enlarged plan view of the MCV of FIG. 4. In FIG. 6, a positioning tool 60 inserted into aperture 49 in retaining arm 50 of the MCV 40. After the MCV has been lifted such that the discoid portion is substantially flush with the capsular bag, the MCV can be manipulated with specifically directed force, or "dialed" into the desired position (for example rotational positioning as indicated by the arrows). While FIG. 6 shows apertures 47 and 49 as relatively narrow substantially oblong or substantially rectangular slits, the apertures could be any useful configuration. For example, as shown in FIG. 7, apertures 76, 78 in substantially teardrop-shaped retaining arms 72, 74 respectively of MCV 70 are substantially circular in shape. The dotted line 82 represents the periphery of MCV 70, which is located under the capsular bag 80 into which the MCV 70 has been implanted through the capsulorhexis 84 made in capsular bag 80. The discoid portion of MCV 70 therefor has a diameter greater than the diameter of the opening 84 in bag 80.

FIGS. 8 and 9 show the MCV 42 of FIG. 4 positioned within a capsulorhexis opening in a capsular bag 40. Cannula 90 is shown inserted into the capsular bag 40, between the surface of the MCV discoid section 46 and the edge of the capsulorhexis 43. In this position the distal end 92 of the cannula 90 is shown in its proper position inside of the capsular bag 40. FIG. 10 shows the polymeric or other lens material 100 being delivered into the capsular bag 40 through the distal end 92 of the cannula 90.

FIG. 11a shows another embodiment of the present invention where MCV 108 has a discoid portion 110. FIG. 11b is a cross-sectional side view of the MCV 108 of FIG. 11a across line B—B showing the discoid portion 110 divided into a thinner central region 112 and thicker peripheral region 114. Such a thickness profile arrangement in the discoid portion of an MCV can provide the necessary hoop-strength to improve retention while ensuring a flush seal with the anterior surface of the capsular bag.

The MCV device of the present invention is preferably constructed from a flexible, biocompatible elastomer. Preferably, the MCV device of the present invention comprises at least one flexible biocompatible elastomeric, or hydrogel, material comprising a synthetic polymer or a polymer of biological origin. For example, the biocompatible elastomeric material may comprise polymer of biological origin, such as a collagen, a collagen-derivative, an amniotic membrane, a cross-linked sodium hyaluronate compound, or mixtures thereof. The biocompatible elastomeric material may comprise at least one synthetic polymer selected from the group consisting of a urethane, a silicone, end-group polymerizable poly-dimethylsiloxanes, poly-dimethylsiloxanes that contain polymerizable groups along and within the chain, and a cross-linkable dimethyldiphenylsiloxane, hydrogels, examples of which are poly-acrylamides, poly-N-vinylpyrrolidones, hydroxyalkylacrylates such as hydroxyethylmethacrylate (HEMA) and mixtures thereof, and poly-tetrafluoroethylene (PTFE), polyethylene (PE), polyethyleneglycol diacrylate (PEGDA), or a mixture thereof. Preferably, the biocompatible elastomer comprises a 10 to 80 Shore A durometer medical grade cross-linkable poly-dimethylsiloxane. More preferred, examples of elastomeric materials include thin silicone membranes cast in a laminar flow hood using a 50 Shore A durometer silicone (Eccosil #4553, Emerson & Cumming, Inc., Canton, Mass., USA), and a medical grade cross-linked poly-dimethylsiloxane (Silastic® silicone elastomer, Dow Corning, Midland, Mich., USA). Even more preferably, the biocompatible elastomer comprises a biodegradable material, for example, a material capable of biodegradation upon photoactivation.

In one embodiment, the MCV device of the present invention comprises an elastomer that is transparent to UV radiation having a wavelength of from about 300 nm to about 1100 nm, and preferably from about 300 nm to about 400 nm to allow photocrosslinking of materials, for example, gels or sols, through the MCV device. In another embodiment, the MCV device of the present invention comprises a gel crosslinkable by visible light having a wavelength of from about 400 nm to about 700 nm, or near infrared light having a wavelength of from about 700 nm to about 1100 nm. Such transparent materials permit in situ crosslinking of polymeric materials through the MCV device, thereby avoiding corneal damage from exposure to radiation.

For disposable MCV devices, medical grade polymeric materials such as urethane, cross-linkable poly-dimethylsiloxanes, and cross-linkable dimethyldiphenylsiloxanes preferably may be employed. MCV devices may be manufactured via conventional casting and molding processes, preferably via injection molding, or may be cut and finished from a thin sheet.

According to the present invention, the MCV may be implantable or disposable. Implantable MCVs are those left in place in a biological or synthetic equivalent tissue for an extended period of time, or indefinitely. Disposable MCVs are those used during a procedure and are then removed from their useful location in a biological tissue or equivalent after only a relatively short duration (e.g. from immediately following the procedure up to several weeks following a procedure).

Preferably the one-piece MCV device is made of one continuous elastomer. Because the MCV of the present invention is an integral, unitary, one-piece structure, the bonding of separate pieces is not necessary. This eliminates the need for potentially toxic adhesives, and simplifies the manufacturing process since no time-consuming and potentially imprecise joining steps are needed. The integral, one-piece nature of the MCV allows for greater precision since a one-piece molded or "cut out" MCV insures precise, repeatable orientation of the retainers relative to the discoid portion. The one-piece MCV of the present invention makes manipulation, placement, retrieval and removal more assured since there is no chance of the retainer feature separating from the body, or discoid section of the one-piece MCV. The greatest torsional forces placed on the MCV during implantation, placement and removal generally occur at the area of interface where the proximal end of the retainer meets the discoid portions. Therefore, the one-piece MCV of the present invention provides a device having significantly greater strength and safety than two-piece designs.

In addition, the one-piece MCVs of the present invention, having varying configurations with respect to the orientation of the retainers on the discoid portion, as well as the dimension of the MCV itself, can be produced and inventoried until their use is desired by the practitioner. Certain types of incisions, or patients with particular requirements due to anatomical parameters may require a MCV having the retainers positioned in a certain way. In this way, the one-piece MCV of the present invention can be manufactured across a broad spectrum of differing retainer features (e.g. differing angles, retainer length, width, etc.) to facilitate their proper use across a diverse patient population. Once again, the present invention allows for enhanced reproducibility, which would be essential for inventoried MCVs having specific, desired properties.

According to the present invention, the discoid portion is itself flexible and may remain as an implant within the capsular bag under certain circumstances. Such circumstances include, inter alia, the injection into the capsular bag of a gel designed to not fully polymerize, introduction of a gel which was intended, but failed to fully crosslink upon curing, and introduction of a viscous liquid or gel that firmly sticks to the MCV device. Such implantable MCV devices comprise biocompatible implant grade materials.

After implantation of the MCV device of the present invention, and injection therethrough of a capsular filling material, the flexible retainers may be severed from the flexible discoid portion member, typically using microscissors. The severed flexible retainers are then removed from the eye. Therefore, according to the present invention, the one-piece MCV has improved characteristics that assist the practitioner. Specifically, with respect to severing and removing the retainers from the MCV, the apertures preferably located at the distal end of the retainer enable the practitioner to more easily grasp, orient and, if necessary remove the retainer, or the entire MCV without risking premature or unwanted separation of the retainer arm from the MCV, or otherwise damaging the MCV.

The physicochemical properties of the material to be injected into the capsular bag will influence the choice of material for a given MCV device. Ideally, the one-piece MCV device of the present invention must comprise a material that will not adhere to viscous fluid or gel injected therethrough. For example, hydrophilic gels such as UV-curable hydrogels, are most compatible with a MCV device manufactured from a hydrophobic material, such as poly-dimethylsiloxane (PDMS). By contrast, a MCV device comprising hydrophilic material, such as a poly-hydroxyethylmethacrylate (pHEMA), is preferred when injecting a hydrophobic fluid or gel into the capsule.

Any material selected for either a disposable or implantable MCV device must be capable of withstanding sterilization procedures. Known procedures include sterilization by autoclaving, gamma irradiation, and ethylene oxide gas, etc. followed by exposure to vacuum, as would be readily understood by one skilled in the field of polymer chemistry.

In addition, ocular surgical procedures utilizing the inventive one-piece MCV devices are safer and more efficient than procedures using conventional methods. The one-piece MCV device of the present invention closes a capsular incision or fissure intraoperatively, permitting injection of toxic therapeutic agents, viscous fluids and gels into the capsular bag without leakage. Capsular lavage with antimitotic agents after placement of the MCV device may reduce postoperative problems associated with cataract surgery, such as opacification and edema.

Still further, using one-piece MCV devices of the present invention to close incisions allows for the improved control of intracapsular pressure and volume during the lens refilling procedures. Pressurization of the capsular bag to levels greater than physiological intraocular pressure also may be achieved using the inventive one-piece MCV device to ensure complete filling of the capsular bag. In addition, implantation of the present one-piece MCV devices will permit adjustments to be made in the required volume of the lens filling material in response to accommodation needs. Closing capsular openings by placement of the present one-piece MCV devices therein avoids postoperative complications generated by under-filled bags, such as, inter alia, hyperopic shift, folds in the posterior capsule, space for lens epithelial cell proliferation and fibrosis. Further, reduced radiation levels may be used in connection with the inventive one-piece MCV device to crosslink materials more slowly than with traditional ocular treatment modalities.

The one-piece MCV device of the present invention further assists practitioners relative to their surgical protocols. For example, ophthalmic surgeons need only a single incision and use of one hand to insert the one-piece MCV devices. Once the one-piece MCV device is seated, all further intraocular manipulations may be accomplished using one hand, including injection of fluids and gels into the capsular bag, irradiation of crosslinkable filler materials with a fiber optic light source, and the like. No interference with iris motion occurs when using one-piece MCV devices because the inventive devices essentially eliminate protrusion of crosslinked gel. Additionally, the inventive one-piece MCV devices permit lavage of the anterior chamber and permit the easy removal of small air bubbles, lens epithelial cells and other unwanted structures (e.g. adherent lens cortex, nucleus particles), debris and material, from the capsular bag.

Procedures designed to refill the eye lens, correct presbyopia, and treat cataracts may be improved when conducted using one-piece MCV devices according to the present invention. Further uses of the inventive one-piece MCV devices include use as temporary patches for small corneal perforations, as well as patches or valves to fill perforations in non-ocular structures, such as organs, blood vessels, other body tissues, etc.

With regard to the capsulorhexis used, as shown in FIGS. 8–10, the one-piece MCV of the present invention prevents fluid or gel leakage from the capsular bag, such as would occur when inserting cannula into the capsular bag between the discoid portion and retainers. Upon insertion, a cannula is compressed between the flexible anterior capsular wall of the anterior capsule and the one-piece MCV device. Upon removal of cannula 90, the retainer arms 48, 50 of the MCV device 42 compress the discoid portion 46 against the interior surface of the capsular bag to seal the capsular bag 40, trapping or sealing injected fluids or gels in the bag. Sealing the capsule opening from the surrounding environment enables, for example, safer and more efficient endocapsular treatment modalities, such as the introduction of anti-proliferative or cytotoxic compounds to retard or eliminate epithelial proliferation in cataract patients. Thus, introduction of anti-proliferative or cytotoxic agents, such as 5-fluorouracil and water, according to the invention may prevent postoperative capsular opacification. The present MCV device also permits the endolavage of dead cells and debris from the capsule. Additionally, the MCV device allows the safe injection of a UV curable polymer into the capsule and subsequent in situ crosslinking by directed exposure to UV light by a fiber optic UV source inserted into the eye through the MCV device.

In one embodiment, the use of the one-piece MCV of the present invention is contemplated as a delivery device for therapeutic agents including pharmaceuticals. In such an embodiment, the MCV is impregnated with a therapeutic agent that is then delivered to the eye such as through leaching or osmotic action. The therapeutic agent may be soluble in an aqueous or saline solution having a salinity level similar to that of tears that would, for example, predictably wash over the MCV at predetermined intervals. In certain instances, if desired, it is further contemplated that a portion of the impregnated MCV itself dissolve, thereby releasing the therapeutic agent. In a further instance, release of the therapeutic agent may be facilitated by the use of radiation, such as, for example, by the use of photo-biodegration.

Capsular filling material may be added or removed via injection or aspiration through the MCV device to adjust the refractive power of the capsular filling material. Adjustment of the refractive power of the de novo lens formed from the capsular filling material may be accomplished during lens replacement surgery, or at some point in time after surgery if an implantable MCV device is used. In such circumstances, it is therefore understood that the MCV acts as a seal as well as a valve. Following insertion, the MCV device may optionally be removed from the eye. Removal would be desirable when, for example, a lens refilling procedure is completed and no further manipulation of the lens capsule is anticipated.

To fit the different sizes of capsulorhexis openings, typically about 0.7 mm to about 1.5 mm in diameter in the peripheral capsular bag, the one-piece MCV device of the present invention may be engineered to a variety of dimensions. Preferably, the discoid portion is a thin, substantially circular disc having a thickness of from about 0.010 mm to about 0.150 mm, and more preferably from about 0.02 mm to about 0.08 mm.

In addition, the discoid portion may be configured such that the circular periphery is thicker than the more central region. This intentional, comparative central "thinning" of the central region of the discoid portion is achieved to permit the discoid portion of the MCV to "pop" outwardly slightly from the eye when the capsule is filled, potentially creating less pressure or distortion to the region. This modified configuration also allows the thickened periphery of the discoid portion to give better "hoop strength" and peripheral intensity to the discoid portion and otherwise impede extrusion as the capsule fills.

Likewise, the retainers may be substantially flat or may be irregularly shaped. Preferably the retainers are very thin and substantially rectangular, crescent shaped, half-moon shaped, oblong, teardrop-shaped, "v"-shaped, etc. and have a thickness of preferably from about 0.010 mm to about 0.150 mm, and more preferably from about 0.02 mm to about 0.08 mm.

The discoid portion diameter may range from about 1.0 mm to about 6.0 mm, and preferably ranging from about 1.2 mm to about 1.8 mm. The tip-to-tip length of the retainers is preferably from about 2.0 mm to about 4.0 mm, more preferably from about 0.3 mm to about 1.5 mm in width, and most preferably from about 0.5 mm to about 1.0 mm in width. The apertures present in the distal end of the retainers of the one-piece MCV of the present invention are preferably from about 0.2 mm to about 0.5 mm in width and 1.0 mm to 2.0 mm in length when rectangular, and from about 0.2 mm to 1.0 mm in diameter when circular.

The diameter of a surgical capsulorhexis opening may be assessed using a micro-ruler placed against a patient's cornea, or by using an intraocular gauge, or measured using a microscope with an eyepiece ocular equipped with a reticule. Intraocular gauges are typically round, smooth, pin-like devices having length marks thereon, suitable for direct placement against the lens capsule surface. Measurement errors of about 10% may be incurred due to corneal refractive power, depending upon the location of the capsulorhexis in relation to the cornea, as well as the positioning of the ruler on the cornea (parallax). Errors are minimized when using the aforementioned intraocular gauge.

The one-piece MCV device is preferably curved to fit the quasi-spherical shape of the capsule inner and outer surface. The retainers are preferably arciform in shape to conform to the pupillary margin and to avoid contact with the iris periphery during surgery. In one preferred embodiment, shaping of the one-piece MCV device preferably may be achieved using molding jigs as would be readily understood by one skilled in the field of molding polymeric materials or, preferably, using a non-contact laser photo-ablating instrument such as the Fluoride (157 nm) excimer laser or the Argon-Fluoride (193 nm) excimer laser. Insertion of the MCV device is preferably accomplished employing toothless, smooth jawed micro-forceps.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

Although specific terms are employed herein, they are used in a generic and descriptive sense only and not for purposes of limitation.

What is claimed is:

1. A one-piece capsulorhexis device for insertion in a lens capsule, comprising:
    a unitary flexible discoid section having a peripheral region and a central region; and
    a plurality of integral retainers, each having proximal and distal ends, said distal end extending radially outward from the central region of the discoid portion,
    wherein the peripheral region of the discoid section is constructed to be positioned along an interior surface of a lens capsule and said retainers are constructed to be positioned along an outer surface of the lens capsule such that a wall of a lens capsule is fixedly positioned between the peripheral region of the discoid section and the retainers.

2. The device according to claim 1, wherein the discoid portion is dimensionally in a shape selected from the group consisting of: curved, flat, and circular.

3. The device according to claim 1, wherein the discoid portion is non-circular.

4. The device according to claim 1, wherein the discoid portion has a diameter of from about 1.0 to about 6.0 mm.

5. The device according to claim 1, wherein distal end has a width of from about 0.3 to about 1.5 mm.

6. The device according to claim 1, wherein the retainer has a length of from about 2.0 to about 4.0 mm.

7. The device according to claim 1, wherein the retainer further comprises an aperture in the distal end.

8. The device according to claim 7, wherein the aperture is substantially circular.

9. The device according to claim 1, wherein the device has a thickness of from about 0.010 mm to about 0.150 mm.

10. The device according to claim 1, wherein the device has a curvature that is substantially similar to the curvature of an inner surface of an ocular lens capsular bag.

11. The device according to claim 1, wherein the device is sufficiently flexible to conform to the shape of a surface to which it is applied.

12. The device according to claim 1, wherein the device is made from a biocompatible elastomer.

13. The device according to claim 1, wherein the device is implantable in mammals.

14. The device according to claim 13, wherein the device is removable after implantation.

* * * * *